United States Patent
Held et al.

(10) Patent No.: US 6,325,080 B1
(45) Date of Patent: Dec. 4, 2001

(54) CLEANING OF MEDICAL DEVICES AVOIDING RECONTAMINATION

(76) Inventors: Georg Held, Schloss Ziegenberg, Ober-Moerlen 61239 (DE); Harald Raith, Flurstrasse 20, Tiefenbronn 75233 (DE)

( * ) Notice: Subject to any disclaimer, the term of this patent is extended or adjusted under 35 U.S.C. 154(b) by 0 days.

(21) Appl. No.: 09/247,411

(22) Filed: Feb. 10, 1999

(51) Int. Cl.$^7$ ........................................... B08B 9/02
(52) U.S. Cl. .................... 134/56 R; 134/166 R; 134/169 R; 134/186
(58) Field of Search ............ 134/166 R, 166 C, 134/169 C, 902, 186, 169 R, 56 R, 57 R

(56) References Cited

U.S. PATENT DOCUMENTS

| | | | |
|---|---|---|---|
| 2,788,008 | * | 4/1957 | Wanzer . |
| 4,730,631 | * | 3/1988 | Schwartz . |
| 4,753,258 | * | 6/1988 | Seiichiro . |
| 4,763,678 | * | 8/1988 | Ott ................................... 134/169 C |
| 5,156,813 | * | 10/1992 | Calhoun . |
| 5,186,194 | * | 2/1993 | Kitajima . |
| 5,225,001 | * | 7/1993 | Manni et al. ..................... 134/169 C |
| 5,511,568 | * | 4/1996 | Bowman et al. ................. 134/169 C |
| 5,520,205 | * | 5/1996 | Guldi et al. . |
| 5,845,663 | * | 12/1998 | Han ...................................... 134/186 |
| 5,896,879 | * | 4/1999 | Gross et al. . |
| 5,922,138 | * | 7/1999 | Shindo et al. . |
| 6,004,401 | * | 12/1999 | Staley .................................. 134/186 |
| 6,102,056 | * | 8/2000 | Kotsopey ............................. 134/186 |
| 6,141,812 | * | 11/2000 | Matsuda et al. . |

* cited by examiner

*Primary Examiner*—Frankie L. Stinson
(74) *Attorney, Agent, or Firm*—Ohlandt, Greeley, Ruggiero & Perle, LLP

(57) ABSTRACT

Disclosed is an apparatus for cleaning a medical device, preferably a medical transducer. The cleaning apparatus comprises a receptacle for receiving the medical device, whereby the receptacle comprises an upper inlet for inserting the medical device through the inlet into the receptacle. For cleaning the medical device, the receptacle is filled with a fluid. According to the invention, the cleaning apparatus is provided with an overflow for receiving fluid (purposely) washed over the inlet for cleaning the inlet. After inserting the medical device through the inlet into the receptacle, the inlet is washed over with the fluid, thus cleaning the inlet. A re-contamination of the medical device by touching the inlet during removal from the receptacle can therefore be avoided.

6 Claims, 2 Drawing Sheets

CLEANING OF MEDICAL DEVICES AVOIDING RECONTAMINATION

BACKGROUND OF THE INVENTION

The present invention relates to the cleaning of medical devices in an apparatus with a receptacle for receiving the medical device. The receptacle comprises an upper inlet for inserting the medical device through the inlet into the receptacle. For cleaning the medical device, the receptacle is filled with a fluid.

Reusable medical devices, such as endoscopes, probes, catheters or the like, for at least partly introducing into a patient's body generally have to be cleaned after use and/or before being applied again. The term 'cleaning' as used herein shall comprise any kind of freeing the device from contamination such as cleansing, disinfecting or sterilizing.

Various apparatus for cleaning endoscopes are disclosed e.g. in EP-A-0038168, FR-A-2705896, and DE-A-3334999. U.S. Pat. No. 5,558,841 discloses a washing/sterilizing apparatus for an endoscope comprising a receptacle adapted to receive the endoscope, means for supplying the receptacle with a disinfection fluid, means for supplying the receptacle with a rising fluid, and removing means for removing any fluid from the receptacle.

FIG. 1 depicts an apparatus 5 for cleaning transesophageal echo (TEE) probes 10 as disclosed in EP-A-0862894 by the same applicant and inventors. Transesophageal echo (TEE) cardiography is an established technique in the area of cardiac imaging and involves the insertion of an ultrasound TEE probe into a subject's esophagus to scan the heart from inside the esophagus. For cleaning the TEE probe 10, the TEE probe is inserted through an upper rim 15, as an inlet of a receptacle 20, into the receptacle 20 (such as a tube) of the TEE probe tester 5. The receptacle 20 is provided with a first inlet 30 for supplying a disinfection fluid into the receptacle 20, a second inlet 40 for supplying a rinsing fluid into the receptacle 20, and a first outlet 50 for removing any fluid from the receptacle 20. The receptacle 20 might further be coupled with an insulation tester 60 providing a first contact 70 within the receptacle 20 and a second contact 80 to be connected with an electrical shielding 90 of the TEE probe 10.

The first inlet 30 may be coupled via a first controller 100 to a first tank 110 containing the disinfection fluid, the second inlet 40 may be coupled via a second controller 120 to a second tank 130 containing the rinsing fluid, and the first outlet 50 may be coupled via a third controller 140 to a third tank 150 for receiving the disinfection fluid and/or the rinsing fluid. The third tank 150 may also receive only the rinsing fluid, and the disinfection fluid is removed back into the first tank 110 and may be exchanged occasionally, e.g., after 10 days. The receptacle 20 may also comprise a fourth outlet coupled to a fourth tank for receiving the disinfection fluid after use. More details and embodiments of the apparatus 5 are readily applicable from EP-A-0862894.

Although the TEE probe tester 5 of FIG. 1 provides an excellent tool for cleaning medical devices, it has been proved to become difficult to insert the medical devices into the receptacle 20 without touching the rim 15. This, however, might lead to a contamination of the rim 15 and thus to a re-contamination of the medical device 10 when it touches the rim 15 during removal from the receptacle 20 after being cleaned.

SUMMARY OF THE INVENTION

It is therefore an object of the invention to provide an improved and safer cleaning of medical devices avoiding a re-contamination of the medical devices.

The object is solved by the independent claims. Preferred embodiments are shown by the dependent claims.

According to the invention, the cleaning apparatus is provided with an overflow for receiving fluid (purposely) washed over the inlet for cleaning the inlet. After inserting the medical device through the inlet into the receptacle, the inlet is washed over with the fluid, thus cleaning the inlet. A re-contamination of the medical device by touching the inlet during removal from the receptacle can therefore be avoided.

The overflow is preferably situated on an outside wall of the receptacle and might be shaped as a funnel around the receptacle. The inlet preferably represents an upper rim of the receptacle. The overflow preferably comprises means, such as an outlet, basin or reservoir, for providing fluid washed-over back into the receptacle or into a container for receiving used fluid.

BRIEF DESCRIPTION OF THE DRAWINGS

Other objects and many of the attendant advantages of the present invention will be readily appreciated and become better understood by reference to the following detailed description when considering in connection with the accompanied drawings. Features that are or can be built up substantially equally or similarly are referred to with the same reference sign.

DETAILED DESCRIPTION OF THE INVENTION

Figure 1:
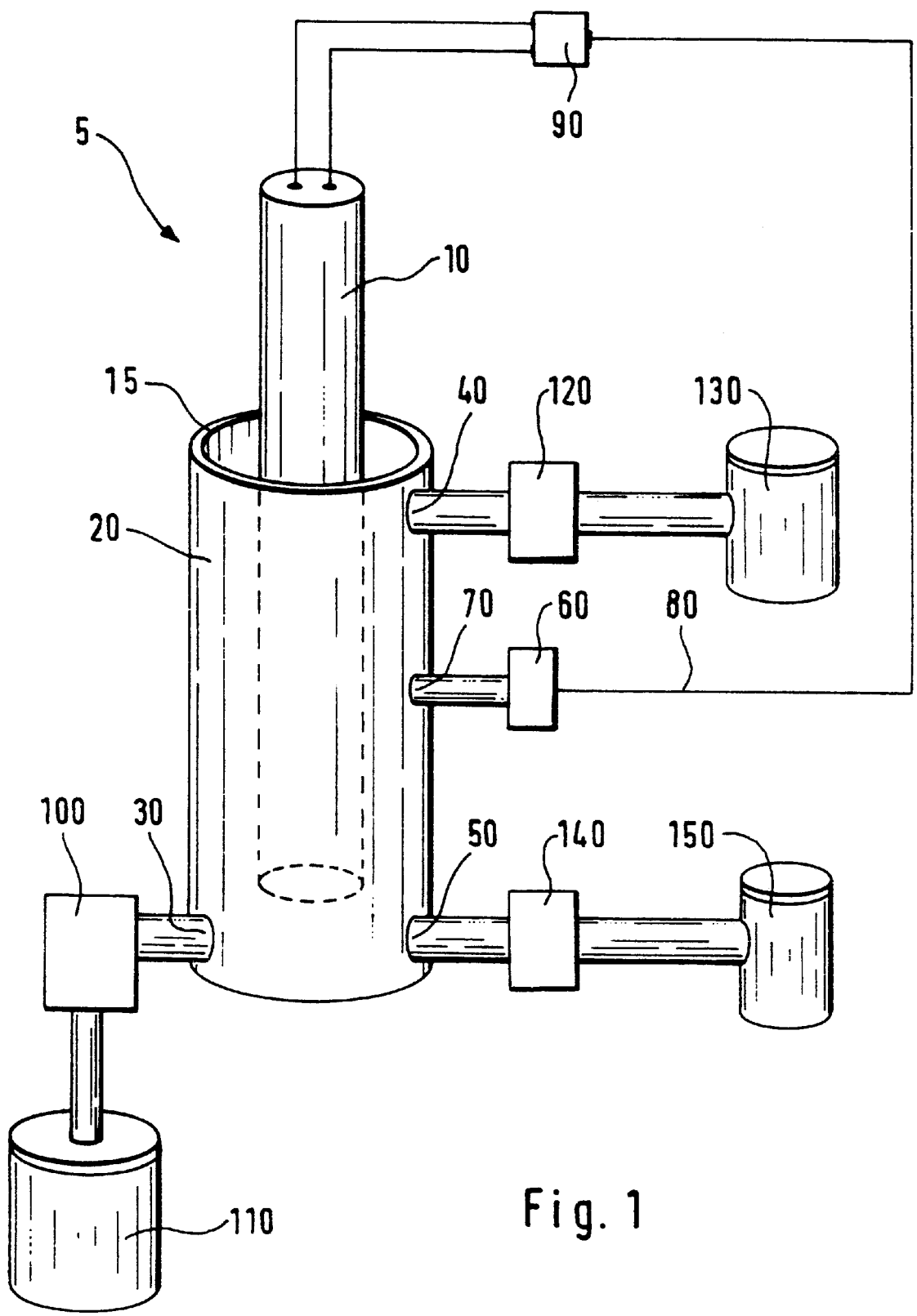
FIG. 1 depicts an apparatus for cleaning transesophageal echo (TEE) probes as disclosed in EP-A-0862894.
Figure 2A:
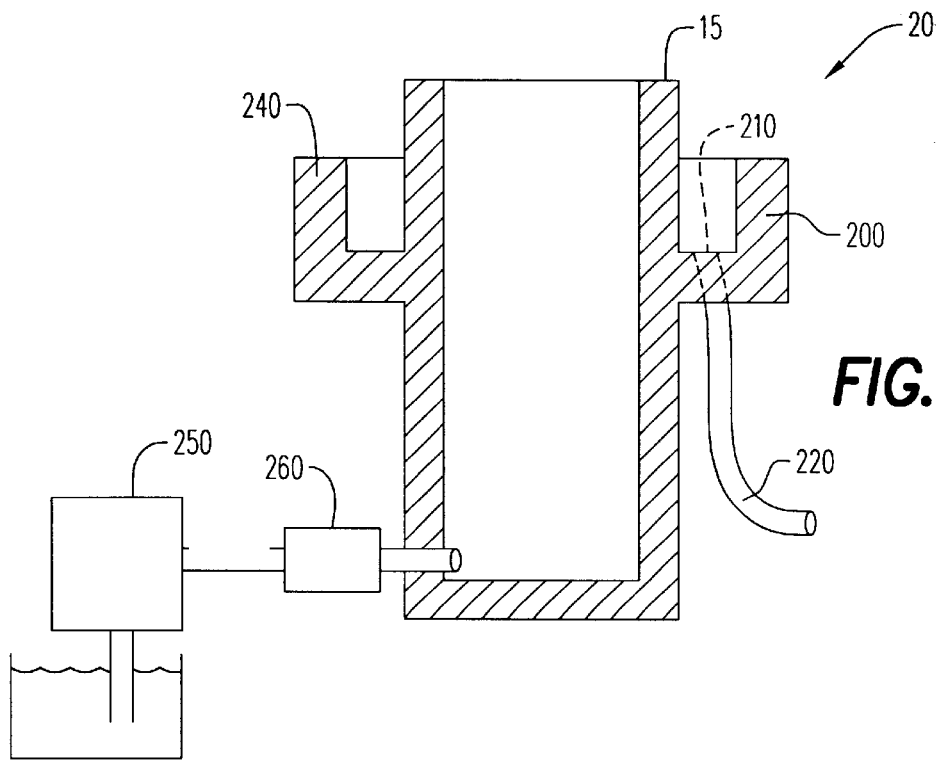
FIGS. 2a and 2b show embodiments according to the invention in cross-sectional views.
Figure 2B:
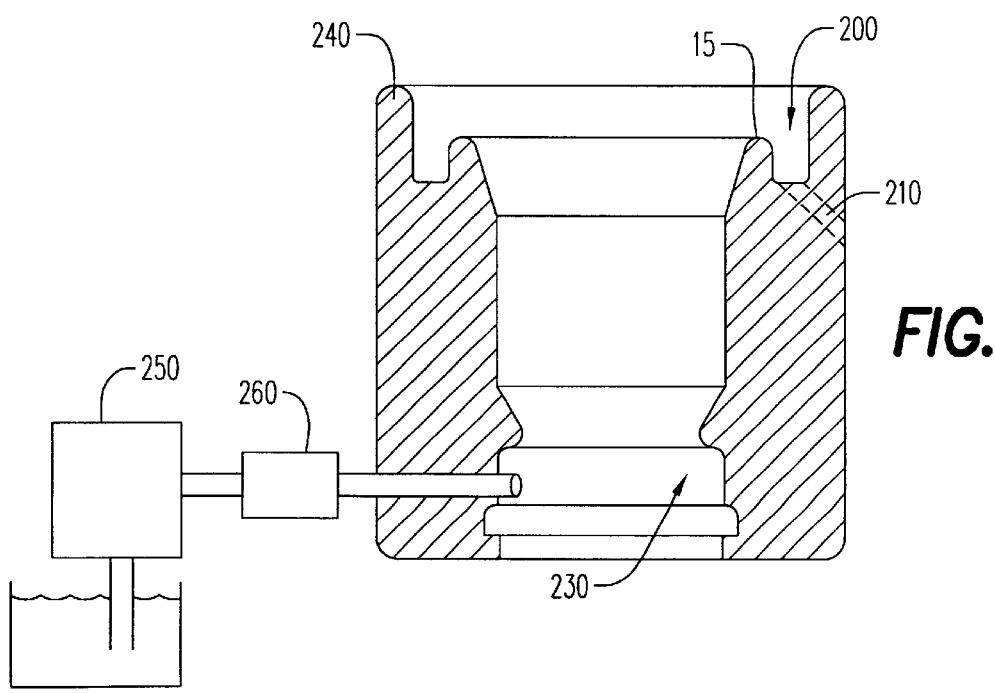

FIGS. 2a and 2b show embodiments according to the invention. The embodiment of FIG. 2a is designed to replace the entire receptacle 20 of FIG. 1, while the embodiment of FIG. 2b is intended to either replace only the upper part of the receptacle 20 of FIG. 1 or to be mounted on top of the receptacle 20. Other features and components of FIG. 1 can be applied accordingly for the purpose of the invention of cleaning a medical device. It is to be understood that the invention, while described hereafter for the apparatus 5 for cleaning TEE probes 10, is not limited to a specific application e.g. for TEE probes, but can be applied for cleaning any kind of medical device. Moreover, the principles of the invention are not limited to the specific embodiment according to FIG. 1, but can be applied to any apparatus with a receptacle, for receiving the medical device, with an upper inlet for inserting the medical device through the inlet into the receptacle.

In the cross-sectional view of FIG. 2a, the receptacle 20 comprises an overflow 200 situated at an outer wall of the receptacle 20. The overflow 200 is adapted to receive fluid washed over the rim 15 for cleaning the rim 15. The overflow 200 can be shaped in any adequate manner allowing to receive the washed-over fluid, e.g. as a funnel, a bucket or the like.

For washing over the rim 15, the receptacle 20 is coupled to or comprises respective fluid moving devices 250 such as one or more pumps. In addition thereto, one or more fluid sensors 260 might be applied for controlling the filling height and speed of the fluid. In a preferred embodiment, the respective fluid moving devices 250 are adapted to wash over the rim 15 for a certain period of time (e.g. 10 to 60 s), preferably at the beginning of a cleaning cycle.

The overflow 200 preferably comprises an outlet 210 allowing to remove (the washed-over) fluid from the overflow 200. The outlet 210 might direct the fluid from the overflow 200 back into the inside of the receptacle 20 (preferably secured by a valve), or e.g. via a tube or hose pipe 220 (or directly) into a container such as the first tank 110 containing the disinfection fluid. It is clear that the outlet 210 represents only an optional feature useful for certain applications. Without the outlet 210, however, it has to be made sure that the overflow 200 is capable to receive the washed-ver fluid. Care has to be taken, in any case, that the overflow 200 will not be flooded by the fluid, and that either a sufficient amount of the fluid can flow off from the overflow 200, or that only a defined amount of fluid will be washed over into the overflow 200. Fluid sensors may be applied to control the amount of fluid (washed over) into the overflow 200.

FIG. 2b depicts another embodiment according to the invention, in cross-sectional view, which is intended to either replace the upper part of the receptacle 20 of FIG. 1 or to be mounted on top of the receptacle 20. In accordance with FIG. 2a, the embodiment of FIG. 2b depicts the overflow 200 situated around the rim 15 which is adapted to receive fluid washed over the rim 15. The overflow 200 further preferably comprises the outlet 210 and corresponding parts attached to the outlet 210 for receiving the fluid from the overflow 200.

For mounting the device of FIG. 2b on top of the receptacle 20 (e.g. according to FIG. 1), it might comprise connecting features 230, such as an adapter or a winding, corresponding to the upper shaping of the receptacle 20.

In a preferred embodiment, the rim 15 is designed to exceed in height an outside wall 240 of the overflow 200, as depicted in FIG. 2a in contrast to FIG. 2b. This reduces the likelihood that the medical device will touch other parts than the rim 15 during insertion into the receptacle 20. However, an appropriate spatial distance between the outside wall 240 of the overflow 200 and the rim 15 and/or an appropriate shaping of the rim 15 and the overflow 200 can also be applied (or in addition thereto).

What is claimed is:

1. An apparatus for cleaning a medical device, the apparatus comprising:

a receptacle for receiving the medical device, whereby the receptacle comprises an upper inlet for inserting the medical device through the inlet into the receptacle, and the receptacle is fillable with a fluid for cleaning the medical device, a fluid moving device for washing fluid over the inlet for cleaning the inlet, a sensor for controlling the speed of said fluid, and an overflow for receiving said fluid washed over the inlet.

2. The apparatus of claim 1, wherein the overflow is situated on an outside wall of the receptacle.

3. The apparatus of claim 1, wherein the overflow comprises means for providing fluid washed-over back into the receptacle or into a container for receiving used fluid.

4. The apparatus of claim 1, wherein the overflow is shaped as a funnel around the receptacle.

5. The apparatus of claim 1, wherein the inlet is an upper rim of the receptacle.

6. An apparatus for cleaning a transesophageal probe, the apparatus comprising:

a transesophageal probe receptacle for receiving said transesophageal probe, whereby the transesophageal probe receptacle comprises an inlet on top of the receptacle for inserting the transesophageal probe through the inlet into the receptacle, wherein the receptacle is fillable with a fluid for cleaning the transesophageal probe, a fluid moving device for purposely washing fluid over an edge of the inlet for at least one of cleaning and disinfecting the inlet, a collecting device for collecting said fluid purposely washed over an edge of the inlet, and a sensor for controlling the speed of said fluid.

* * * * *